United States Patent [19]

Osugi et al.

[11] Patent Number: 5,156,833
[45] Date of Patent: Oct. 20, 1992

[54] POWDER AEROSOL COMPOSITION

[75] Inventors: Takao Osugi, Iwatsuki; Toshihiro Jinno, Ichikawa, both of Japan

[73] Assignee: Lion Corporation, Japan

[21] Appl. No.: 650,070

[22] Filed: Feb. 4, 1991

[30] Foreign Application Priority Data

Feb. 7, 1990 [JP] Japan ................... 2-26202

[51] Int. Cl.$^5$ ................. A61K 9/12; A61K 9/14
[52] U.S. Cl. ......................... 424/46; 424/47; 424/401; 514/786; 514/941; 514/975
[58] Field of Search ............ 424/47, 43, 45, 46, 424/401; 514/941, 975, 786

[56] References Cited

U.S. PATENT DOCUMENTS 4,183,911  1/1980  Smithies et al. ............... 424/47 X

*Primary Examiner*—Thurman K. Page
*Attorney, Agent, or Firm*—Lorusso & Loud

[57] ABSTRACT

A powder aerosol composition is disclosed which includes a powder, a liquefied propellant gas selected from liquefied petroleum gases and liquefied natural gases, and a nonionic surfactant which is substantially insoluble in the liquefied propellant gas.

4 Claims, No Drawings

POWDER AEROSOL COMPOSITION

BACKGROUND OF THE INVENTION

This invention relates to a powder aerosol composition containing a powder homogeneously suspended in a liquefied petroleum gas or liquefied natural gas serving as a propellant.

Powder aerosol compositions are now utilized as an anti-perspirant, a body lotion, a foot spray, or the like cosmetic application. These aerosol compositions generally contain a powder, such as talc, for improving feelings of usage, a powder anti-perspiration ingredient, such as aluminum chloride, and a propellant and are charged in valved containers. In use, the aerosol composition is dispensed through the valve as an aerosol.

While fluorocarbons have been used as the propellant, recent trend is toward the use of a liquefied petroleum gas or a liquefied natural gas for reasons of environmental pollution caused by fluorocarbons. The use of a liquefied petroleum or natural gas propellant, however, has been found to pose a problem because the powder tends to aggregate in the liquefied propellant so that the valves are clogged during use.

SUMMARY OF THE INVENTION

It is, therefore, an object of the present invention to provide a powder aerosol composition which is in the form of a homogeneous suspension and keeps the suspended state for a long period of time without forming aggregates of the powder.

Another object of the present invention is to provide a powder aerosol composition of the above-mentioned type which does not cause the clogging of valves of containers through which the composition is dispensed as an aerosol.

In accomplishing the foregoing objects, the present invention provides a powder aerosol composition which includes a powder, a liquefied propellant gas selected from the group consisting of liquefied petroleum gases and liquefied natural gases, and a nonionic surfactant which is substantially insoluble in the liquefied propellant gas.

Other objects, features and advantages of the present invention will become apparent from the detailed description of the preferred embodiments of the invention to follow.

DESCRIPTION OF PREFERRED EMBODIMENTS

The powder to be used in the present invention may be, for example, a material of powder and/or a powder antiperspirant.

Both organic and inorganic powder may be used as the material of powder. Illustrative of suitable materials of powder are talc, kaolin, zinc oxide, titanium oxide, magnesium oxide, bentonite, silica, mica, zeolite, magnesium silicate, calcium silicate, petaloid silica, titanium mica, silk, nylon, polyethylene, polystyrene, polymethylmethacrylate and crosslinked polyacrylic acid. These substances may be used by themselves or as a mixture of two or more. The material of powder generally has an average partcle size of 1-50 $\mu$m, preferably 3-30 $\mu$m and is generally used in an amount of 0.1-10% by weight, preferably 0.5-5% by weight based on the total weight of the composition.

It is preferred that the material of powder be formed from secondary particles each of which is an aggregate of primary particles, for reasons of attaining non-stickiness on the skin and of improving dry feeling on the skin.

Such a material of powder having a secondary structure is disclosed in detail in Japanese Published Unexamined Patent Application (Tokkyo Kokai) No. 63-130535 and may be obtained by aggregating primary particles having an average particle size of 0.1-10 $\mu$m. Secondary particles having a surface area of 50-200 $m^2/g$, preferably 80-180 $m^2/g$, a pore volume of 0.01-10 ml/g, preferably 0.05-5 ml/g, and an average particle size of 1-50 $\mu$m, preferably 3-30 $\mu$m and formed of silicic acid anhydride (silicon dioxide) or titanium oxide are preferably used. By using a material of powder with such a secondary structure, non-stickiness and dry feeling on the skin may be advantageously obtained. This is considered to result from the porous structure of the secondary particles formed between the primary particles. The space defined between the primary particles serves as a passage through which sweat on the skin surface may be removed by evaporation. The use of a material of powder with a secondary structure is also advantageous because the skin applied therewith is not whitened. This is probably attributed to relatively high light permeability of the secondary particles.

The powder anti-perspirant may be, for example, astringent single salts such as aluminum chloride, aluminum oxychloride, basic aluminum bromide, aluminum sulfate, aluminum chlorohydrate, aluminum zirconium chlorohydrate, zinc sulfate, aluminum phenolsulfonate, phenolsulfonate and basic aluminum zinc lactate, and complexes of these single salts with glycol, amino acid or the like complex-forming compounds. These substances may be used by themselves or as a mixture of two or more. The anti-perspirant generally has an average particle size of 1-50 $\mu$m, preferably 3-30 $\mu$m, and is generally used in an amount of 0.2-10%, preferably 0.5-5% based on the total weight of the composition.

The liquefied propellant to be used in the present invention is a liquefied petroleum gas or a liquefied natural gas. The liquefied petroleum gas and natural gas may be used in conjunction with one or more other propellants such as liquefied butane or the like liquefied hydrocarbons, if desired. The liquefied propellant is generally used in an amount of 80-98%, preferably 85-96%, based on the total weight of the composition.

The nonionic surfactant to be used in the present invention is a liquid which is substantially insoluble in the above-described liquefied propellant. Nonionic surfactants having a solubility of 1.0 g or less at 25°C., preferably 0.5 g or less at 25°C., in 100 g of the liquefied propellant may be suitably used. Examples of the nonionic surfactants include (1) polyesters of long chain fatty acids with glycerin having one or more oxyalkylene groups, such as polyoxyethylene glyceryl triisostearate (2) polyesters of long chain fatty acids with hardened castor oil, such as polyoxyethylene triisostearic acid ester of hardened castor oil (3) fatty acid esters of sorbitol having one or more oxyalkylene groups and (4) mixtures thereof. The nonionic surfactant is generally used in an amount of 0.1-10% preferably 0.5-5% based on the total weight of the composition. When the powder is mixed with the liquefied propellant gas, the nonionic surfactant is adsorbed or absorbed on the surfaces of the powder to improve the suspensibility of the powder in the liquefied propellant gas.

The aerosol composition according to the present invention may further contain one or more additives such as oils, germicides, inclusion compounds (e.g. cyclodextrin), vitamins, amino acids, anti-inflammatory agents (e.g. glycyrrhizinic acid), cooling agents (e.g. menthol), natural drugs and perfumes. Illustrative of suitable oils are fluid paraffin, isopropyl myristate, octyl myristate, dodecyl myristate, isopropyl palmitate, diisopropyl adipate, diisobutyl adipate, silicone oil, avocado oil, hohoba oil, lanoline, cetyl 2-ethylhexanoate, butyl isostearate, triethyl citrate, acetyltributyl citrate, butyl phthalate and cetyl octanoate. Illustrative of suitable germicides are benzalkonium chloride, isopropylmethylphenol, triclosan, trichlorocarbanilide, chlorohexidine hydrochloride and benzethonium chloride.

The following examples will further illustrate the present invention.

EXAMPLE

Powder aerosol compositions (Nos. 1-11) were prepared using a liquefied peteroleum gas as a propellant, 0.1% by weight of a perfume, and anti-perspirants, materials of powder, oils and nonionic surfactants as shown in Table below in amounts shown in Table below. Each of the compositions was tested for its suspensibility and valve-clogging tendency. The results are summarized in Table below.

The test methods are as follows:

Suspensibility Test

The sample aerosol composition is charged in a transparent glass container and is shaked. Then, the container is allowed to quiescently stand for a predetermined period of time. Suspensibility is evaluated based on the following ratings:
A: Good suspensibility
B: No good suspensibility
C: Poor suspensibility

Clogging Test

The sample aerosol composition is charged in a valved container, shaked and allowed to stand at 40° C., for 3 months. The composition is sprayed once a week to check whether or not the valve is clogged. Clogging tendency is evaluated based on the following ratings:
A: No clogging for 3 months.
B: Valve is clogged within 3 months.

In Table, the abbreviations are as follows:
ACH: Aluminum chlorohydrate
IPM: Isopropyl myristate
IPP: Isopropyl palmitate
CMP: Cyclic methylpolysiloxane
PGT: Polyoxyethyleneglyceryl triisostearate (ethylene oxide addition mol number: 20)
PCT: Polyoxyethylene hardened castor oil triisostearate (ethylene oxide addition mol number: 20)
PNE: Polyoxyethylene nonylphenyl ether (ethylene oxide addition mol number: 2)

The silica used in this example is spherical silica micro bead (manufactured by SHOKUBAI KASEI K. K.) having a secondary structure. Compositions Nos. 1–8 are those of the present invention while Compositions Nos. 9–11 are comparative ones.

| Composition No. | 1 | 2 | 3 | 4 | 5 | 6 | 7 | 8 | 9 | 10 | 11 |
|---|---|---|---|---|---|---|---|---|---|---|---|
| Anti-perspirant | | | | | | | | | | | |
| ACH | 2.0 | 2.0 | 2.0 | 2.0 | 2.0 | 2.0 | — | — | 2.0 | 2.0 | 2.0 |
| Aluminum chloride | — | — | — | — | — | — | 2.0 | 2.0 | — | — | — |
| Powder Substrate | | | | | | | | | | | |
| Talc | 2.5 | — | — | 2.5 | 2.5 | 2.5 | — | — | 2.5 | 2.5 | 2.5 |
| Silica | — | 2.5 | — | — | — | — | 2.5 | 1.5 | — | — | — |
| Kaolin | — | — | 2.5 | — | — | — | — | 1.0 | — | — | — |
| Oil | | | | | | | | | | | |
| IPM | 3.0 | 3.0 | 3.0 | 3.0 | 3.0 | — | — | 3.0 | 3.0 | 3.0 | 3.0 |
| IPP | — | — | — | — | — | 3.0 | — | — | — | — | — |
| CMP | — | — | — | — | — | — | 3.0 | — | — | — | — |
| Surfactant | | | | | | | | | | | |
| PGT | 2.0 | 2.0 | 2.0 | 4.0 | — | 2.0 | 2.0 | 1.0 | — | — | — |
| PCT | — | — | — | — | 2.0 | — | — | 1.0 | — | — | — |
| PNE | — | — | — | — | — | — | — | — | — | 2.0 | 5.0 |
| Suspensibility | A | A | A | A | A | A | A | A | C | B | B |
| Clogging Tendency | A | A | A | A | A | A | A | A | C | C | C |

As will be evident from the results shown in Table above, the use of nonionic surfactants (PGT and PCT) which are insoluble in liquefied petroleum gas provides powder aerosol compositions having good suspensibility and free of valve-clogging. A nonionic surfactant (PNE) which is soluble in liquefied petroleum gas, on the other hand, fails to achieve the objects of the present invention.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

What is claimed is:

1. A powder aerosol composition comprising:
    a powder;
    a liquefied propellant gas selected from the group consisting of liquefied petroleum gases and liquefied natural gases; and
    a nonionic surfactant which is polyoxyethyleneglyceryl triisostearate or polyoxyethylene hardened castor oil triisostearate, said surfactant being substantially insoluble in said liquefied propellant gas.

2. A composition as claimed in claim 1, wherein said powder is present in said composition in an amount of 0.1-20% by weight.

3. A composition as claimed in claim 1, wherein the content of said nonionic surfactant is in the range of 0.1-10% by weight.

4. A composition as claimed in claim 1, wherein said powder has an average particle size of 1-50 μm.

* * * * *